United States Patent
Thomson et al.

(10) Patent No.: US 10,846,424 B2
(45) Date of Patent: Nov. 24, 2020

(54) METHOD FOR MULTI-TIERED, RULE-BASED DATA SHARING AND ONTOLOGY MAPPING

(71) Applicant: Medidata Solutions, Inc., New York, NY (US)

(72) Inventors: Justin Thomson, Brooklyn, NY (US); Evan Shore, New York, NY (US)

(73) Assignee: Medidata Solutions, Inc., New York, NY (US)

( * ) Notice: Subject to any disclaimer, the term of this patent is extended or adjusted under 35 U.S.C. 154(b) by 116 days.

(21) Appl. No.: 14/478,860

(22) Filed: Sep. 5, 2014

(65) Prior Publication Data

US 2016/0070758 A1  Mar. 10, 2016

(51) Int. Cl.
*G06F 21/62* (2013.01)
*G16H 10/60* (2018.01)

(52) U.S. Cl.
CPC ......... *G06F 21/6245* (2013.01); *G16H 10/60* (2018.01)

(58) Field of Classification Search
CPC ......... G06F 17/30734; G06F 17/30917; G06F 21/6245; G16H 10/60
See application file for complete search history.

(56) References Cited

U.S. PATENT DOCUMENTS

| | | | |
|---|---|---|---|
| 7,373,338 B2 * | 5/2008 | Thompson | G06F 17/30734 707/690 |
| 7,438,233 B2 | 10/2008 | Leiper | |
| 7,640,267 B2 * | 12/2009 | Spivack | G06F 17/30731 |
| 8,065,166 B2 | 11/2011 | Maresh et al. | |
| 8,306,831 B2 | 11/2012 | Eisenberger et al. | |
| 8,935,804 B1 * | 1/2015 | Clark | G06F 17/30873 726/27 |
| 9,032,544 B2 * | 5/2015 | Shelton | G06F 21/6245 726/28 |
| 9,141,726 B1 * | 9/2015 | McNair | G06F 21/6245 |
| 9,230,134 B1 * | 1/2016 | Grigera | G06F 21/6245 |
| 2004/0117346 A1 * | 6/2004 | Stoffel | G06F 17/30607 |

(Continued)

FOREIGN PATENT DOCUMENTS

| | | | | |
|---|---|---|---|---|
| CA | 2278727 A1 * | 7/1998 | ........... | G06F 16/958 |
| WO | 2012/054932 A2 | 4/2012 | | |

OTHER PUBLICATIONS

The International Search Report and Written Opinion of the International Searching Authority, PCT/US2014/072475, dated May 11, 2015.

*Primary Examiner* — Amresh Singh
(74) *Attorney, Agent, or Firm* — Steptoe & Johnson LLP; Robert Greenfeld

(57) ABSTRACT

A computer-based method for creating enforced, context-specific sharing of ontologically mapped, aggregated medical data includes storing at least one data field in a database as an entity type ontology, receiving context-specific rule configurations corresponding to the entity type ontology, and identifying any conflict between the received context-specific rule and any applicable rule. The context-specific rule configurations include at least one context, one data source, and one entity type ontology data field. If a conflict is identified, the method receives resolution of the conflict and stores the context-specific rule configurations in the database.

11 Claims, 10 Drawing Sheets

(56) References Cited

U.S. PATENT DOCUMENTS

| | | | |
|---|---|---|---|
| 2004/0158455 A1* | 8/2004 | Spivack | G06F 17/30731 |
| | | | 704/9 |
| 2004/0243633 A1* | 12/2004 | Thompson | G06F 17/30734 |
| 2005/0182745 A1* | 8/2005 | Dhillon | G06Q 10/10 |
| 2007/0192140 A1* | 8/2007 | Gropper | G16H 10/60 |
| | | | 705/3 |
| 2008/0250020 A1* | 10/2008 | Madhavan | G06F 17/30734 |
| 2009/0138960 A1 | 5/2009 | Felty et al. | |
| 2009/0254392 A1* | 10/2009 | Zander | G06F 21/6218 |
| | | | 705/50 |
| 2010/0057815 A1* | 3/2010 | Spivack | G06F 17/30731 |
| | | | 707/794 |
| 2011/0202974 A1 | 8/2011 | Leader et al. | |
| 2012/0102502 A1 | 4/2012 | Mathur et al. | |
| 2012/0331567 A1* | 12/2012 | Shelton | G06F 21/6245 |
| | | | 726/28 |
| 2013/0019002 A1 | 1/2013 | Heileman et al. | |
| 2013/0339311 A1* | 12/2013 | Ferrari | G06Q 30/0627 |
| | | | 707/687 |
| 2014/0100875 A1* | 4/2014 | Davis | G16H 10/60 |
| | | | 705/3 |
| 2014/0108046 A1 | 4/2014 | Echeverria Cabrera et al. | |
| 2015/0066522 A1* | 3/2015 | Cane | G06F 19/322 |
| | | | 705/2 |
| 2015/0310575 A1* | 10/2015 | Shelton | G06F 21/6245 |
| | | | 705/325 |
| 2017/0186123 A1* | 6/2017 | Shelton | G06F 21/6245 |

\* cited by examiner

| Home | Inbox | Rules | Settings | PKs | More... | | Sponsor A ▼ |

Refine by | Reset | Data Available to Sponsor A

405 Context Type: Clinical Trial ▼
410 Context: Clinical Trial A ▼
415 Entity Type: Patient ▼
420 Entity: All ▼
425 Date Range: 10/02/13 to 09/14/14
430 Data Sources: Select data sources... ▼
  ☒ EDC Systems
  ☐ EMR Systems
  ☐ Payor Databases
  ☐ Pharmacy Databases
  ☐ Lab Databases
  ☐ Genomic Databases
  Edit data sources...

440 e.g., People in Clinical Trial A 🔍

441 1,500 unique target entities

| 442 Fields | 443 Range of Values | 445 Automatically Accessible | Accessible by Request | Outside Query Context |
|---|---|---|---|---|
| ☒ Name | All People 🔍 | ☒ 0 records | ☐ 200 records | 1,300 records |
| ☒ Weight | 20 lbs ——▲—— 420 lbs | ☒ 500 records | ☐ 400 records | 600 records |
| ☒ Age | 0 years ——▲—— 105 years | ☒ 400 records | ☒ 600 records | 500 records |
| ☒ Gender | ☒ Male ☒ Female | ☒ 300 records | ☐ 800 records | 400 records |
| ☒ Quality of Life | All Surveys ▼ | ☒ 200 records | ☐ 1,000 records | 300 records |
| ☒ Genomics | All Sequences ▼ | ☒ 100 records | ☐ 1,200 records | 200 records |

447 View Results    448 Send Request    449 View/Edit Rules

FIG. 5

Figure 5 — Rule definition interface (500):
- Home | Inbox | ... | Settings | More... | Sponsor A
- *Define rule...* 505
- Rule Name 505: Rule 001
- Requestor(s) 510: Sponsor A
- Context Type 515: Clinical Trial
- Context 520: Clinical Trial A
- Entity Type 525: Patient
- Entity 530: All
- Date Range 535: 10/02/13 to 09/14/14
- *Select data...* 550
  - Data Sources 555: [x] EDC Systems, [ ] EMR Systems, [ ] Payor Databases, [ ] Pharmacy Databases, [ ] Lab Databases, [ ] Genomic Databases, See more...
  - Data Fields 557: [x] Name, [x] Weight, [ ] Gender, [ ] Age, [ ] Quality of life surveys, [ ] Genomic sequence, Edit conditional logic...
  - 540 Remove Duplicates
- *Select actions...* 560
  - Approving Entity: Patient
  - Approval Action: Select action... [x] Automatic, [ ] Manual request
  - 580 Set Data Visibility
- 570 Save

US 10,846,424 B2

METHOD FOR MULTI-TIERED, RULE-BASED DATA SHARING AND ONTOLOGY MAPPING

BACKGROUND

Patient data plays a valuable role in the healthcare and life sciences industries. Physicians and hospitals can use patient data to provide specific diagnoses of diseases, more personalized recommendations of therapies, and tailored disease management programs. Clinical trial sponsors can use patient data to enroll more appropriate participants in clinical trials, more specifically tailor clinical trial protocols, and analyze the effectiveness and safety of their therapies. Researchers can use the data to understand biological, behavioral, and contextual factors affecting patient health outcomes. Government agencies can use patient data to better understand their populations as well as trends for healthcare risks of citizens. Payors, such as insurance organizations, can use this data to manage risk and optimize reimbursements. However, the desire for many organizations to utilize patient data must be balanced with a patient's desire for personal privacy. Patients may have certain medical data they wish to keep private, or provide only to select entities or in certain contexts.

Patients interact with many different organizations over time, including multiple physicians, hospitals, clinical trials, consumer and medical devices, social media, and other non-healthcare organizations. These organizations both generate and consume patient data, but the variety of these organizations often leaves a patient's data segregated into non-overlapping silos. It may be difficult, or impossible in some situations, for applications to leverage data across the silos to obtain a complete picture of a patient's health. Similarly, it may be difficult for patients to manage their personal privacy across these disparate sources.

This problem is not unique to data about patients, but rather extends to any individual or organization about which data are generated. Clinical trial sponsors, for example, may wish to share data about therapies, investigator sites, and patients involved in their clinical trials. However, these sponsors may only wish to share certain fields of data with certain organizations or people, and lack an ability to translate data stored in different systems using different ontologies into a commonly-understood format.

BRIEF DESCRIPTION OF THE DRAWINGS

FIG. 4 is an example querying interface, according to an embodiment of the present invention;

FIG. 5 is an example rule creation interface, according to an embodiment of the present invention;

Figure 1:
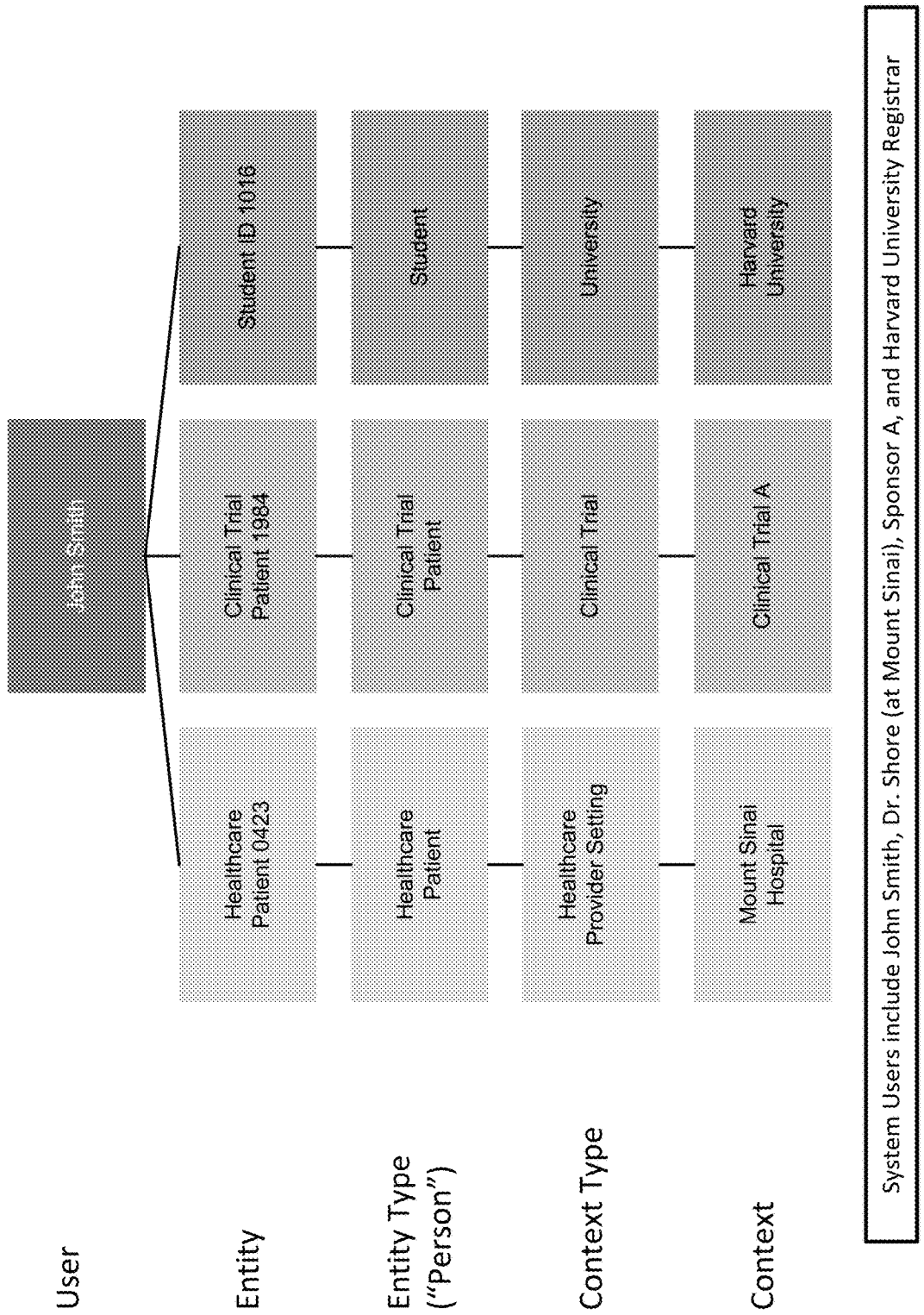
FIG. 1 is an example context entity map, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Although embodiments of the system will be discussed herein in the context of clinical trials and patient medical records, the inventive features disclosed herein are designed to be applicable to many other areas and fields of use. These areas may include, without limitation, manufacturing, supply chain, financial, personal health, educational, and business-oriented data records, among others.

In many cases, patients do not have a consolidated location to manage their healthcare identity and distribution of sensitive information. Patients also do not have the ability to provide different levels of access permissioning to different entities for different elements of medical information. These patients would benefit from having more complete control of their personal healthcare data and overall security of their identity.

Existing data permissioning protocols are binary, as they allow a user only to dictate whether or not the user's data can be accessed. Existing systems generally toggle data access "on" or "off" based on a consent form signed by a user, or the user's individual selection. Existing data permissioning protocols are not granular enough to accommodate data-specific, context-specific, requester-specific, and time-sensitive permissioning to facilitate total control over one's data identity. Further, existing data permissioning protocols fail to provide multi-tiered permissioning rules that automatically control access to specific data in specific contexts. Existing systems also typically do not enforce a common ontology, but only facilitate the exchange of data in the native structure of each data source.

Further, the manner in which individuals control privacy and sharing permissions can be fragmented and/or manual. When government agencies create laws, compliance is often managed through human oversight. Different organizations may enter into data sharing consent agreements with individuals that are usually captured on paper. However, these consent agreements and laws may not accommodate individual patient preferences regarding what types of data are shared to whom and in what contexts. Additionally, there is no over-arching framework that is aware of all laws, consent agreements, and individual preferences that are relevant for a given individual.

Embodiments of a computer-based system have been developed that protect sensitive data and allow an individual or organization to have control over its associated data. Such systems protect sensitive data through the use of multi-tiered, rule-based data access permissioning filters, such as filters that enable or limit another user's access to data based on contexts, entity types, date ranges, and data sources. Such systems allow an individual or organization to customize, at a granular level, specifically what information a requesting user may access under various conditions. Within this specification, a "user" may be a person or organization that utilizes the system, and may act as a data provider, a data requester, and/or rule creator, for example. Users may also conduct other activities such as communicating, or sending and receiving payments, for example. Within this specification, an "entity" may be a data construct representing something about which data are generated and can be queried in the system. Users may be represented as entities in the system when data are generated about them.

FIG. 1 illustrates an example relationship between users, entities, and contexts as applied to an embodiment of the present invention. Users may have complete control over what information is shared to whom, by whom (as users may delegate sharing responsibility to another user), and in what contexts (e.g., data may be shared between a user and Sponsor A in clinical trial A but not in clinical trial B; or, before the year 2021 but not after).

Permissioning filters may be based on rule tiers to enable data sharing in specific contexts. In some embodiments of the system, there may be three rule tiers: laws, consent agreements, and user-defined individual preferences. Contexts may include any combination of attributes, including (but not limited to) querying entity (e.g., "sponsor A"), data fields (e.g., "weight"), data context (e.g., "clinical trial A"), conditional data fields (e.g., weight >200 lbs.), data sources (e.g., Electronic Data Capture ("EDC") systems), date of query, or date of data being queried, for example. Access to a portion of a user's data may be granted by the user manually with each query or automatically via a global or context-specific default setting.

Embodiments of the system may allow a user to manage access to the user's sensitive information at a granular level using multi-tiered permissioning by both user type and data type. Where time-bound agreements or laws apply, requesting users are subject to these temporal conditions. Additionally, users may select temporal limitations for particular data fields, for example, by providing access to information for a predetermined period of time, or by making information public after a predetermined period of time has passed. A user's information may include data such as (but not limited to) operational, financial, and clinical/personal health data. Sources of operational data may include hospital systems, manufacturing plants, and supply chains. Financial transaction data may include site payments in clinical trials, payor reimbursements, and personal shopping or credit history. Sources of clinical or personal health data may include medical records, medical images, medical devices, mobile or other consumer devices, genomic sequences, lab data, pharmacy/prescriptions, and quality-of-life surveys. Accordingly, the system described herein can also be used in a variety of data contexts.

In some embodiments, the system may locally store user medical information and other types of data, and may distribute the data pursuant to permissioned requests. In these embodiments, the system may be used to manage data within an organization where requesting users seek access to the organization's data resources. In other embodiments, the data may be stored remotely, or accessed from its original source, while the system operates as a broker to share data based on specific, multi-tiered user permissions, including requests by entities that are external to a user's original data resources. In these embodiments, the system may manage data from disparate sources in the form of an aggregator or data management service provider by aggregating data among users that participate in the service provider's program. Embodiments of this system may comprise a distributed database among multiple sources, or a local database stored locally at a single source. In other embodiments, the system can be co-configured with a billing system to charge fees based on requests or data accessed.

Embodiments of the system may enable or restrict data sharing that is compliant with applicable laws, consent agreements, and individual user preferences. The system also may convert written laws or executed consent agreements regarding data sharing, for example, into structured hierarchical rules understood by the system to determine data-sharing permissioning. In some embodiments, the process of converting written laws or consent agreements may be a manual process. For example, individuals may read the written laws or consent agreements and enter them into the system by coding rules that may be used to determine data-sharing permissioning. In some embodiments, the system may be configured to receive and review written laws or consent agreements and automatically convert these laws or agreements into rules, such as by using programs configured to parse structured text. The system can be used to assign these rules into a structured hierarchy and populate into options selectable by certain users to govern data-sharing permissioning.

In some embodiments, the system may be configured to use laws and rules identified and understood by the system in order to create consent agreements. These consent agreements can be created, such as by data providers, and distributed to patient users for approval and/or signature through the system. System-created consent agreements may be used to allow more advanced and streamlined processes for obtaining informed consent in medical and clinical settings. This may result in less paperwork, fewer user and entity overhead costs, and faster enrollment in clinical trials, for example.

In some embodiments, a user may desire to add a data field to the system, in order to share and/or query this data. The system may be configured to suggest the names and descriptions of similar fields already in the system. This may be accomplished, for example, using machine learning algorithms such as tf-idf (term frequency-inverse document frequency) scores or string distance. As described further herein, in some embodiments the system may link data fields when the data providing user accepts system data mapping suggestions or creates their own mappings. If the system cannot determine a mapping for the potential new data field, or if the data providing user elects not to link the data field to any other, a new field may be created. In some embodiments described further herein, for each user, the system may also require that certain fields be entered using a standardized ontology specific to that entity. An ontology is a controlled vocabulary describing entities, whereby there is a defined relationship among distinct data fields related to those entities. For data to be shared with other users, the data fields must be linked to an ontology and rules must be applied to the ontologically-mapped fields. The system may also be configured to require certain information be provided about a user in order for that user to be added to the system.

In some embodiments, certain data providers, such as electronic medical devices (for example), may access the system to consume and/or contribute data. These devices may consume user data to make computations relevant to the device's medical purpose in conjunction with its general function. Additionally, these devices may also contribute data they measure or generate so that other users in the system may access it. Accordingly, embodiments of the system may enable bi-directional information sharing governed by multi-tiered granular permissioning.

Embodiments of the invention will now be described with reference to the accompanying figures. In embodiments disclosing modular elements, it should be understood that modules may be structurally distinct or functional units. Each module may comprise a component of a larger integrated application. Database elements may comprise separate or combined logical entities.

Figure 2A:
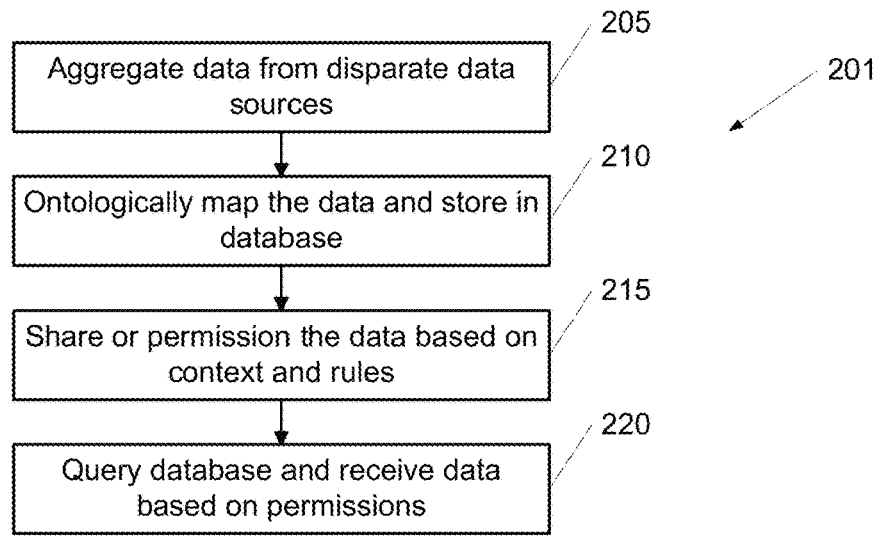
FIGS. 2A-2B are flowcharts illustrating embodiments of the present invention.
Figure 2B:
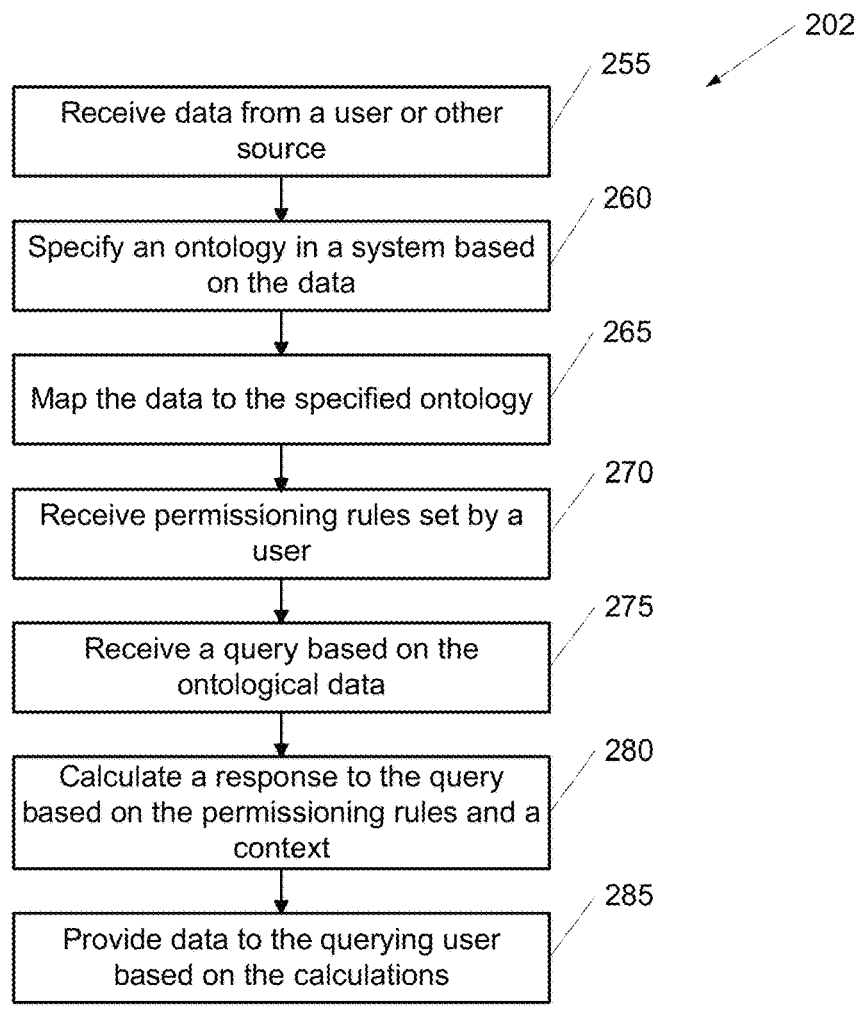

Reference is now made to FIGS. 2A and 2B, which are flowcharts 201 and 202 illustrating embodiments of the present invention. In operation 205, the system may aggregate data from disparate data sources. In operation 210, the system may ontologically map the data and store the data in a database. In operation 215, a user may share or permission the data based on context and rules. In operation 220, a querying user queries the database and receives data based on the permissions.

FIG. 2B shows another embodiment of system 100. In operation 255, the system receives data from a user or other source. In operation 260, the system specifies an ontology based on the data. In operation 265, the system maps the data to the specified ontology. In operation 270, the system receives permissioning rules set by a user, where the rules may be based on the context in which the data exist. In operation 275, the system may receive a query from a querying user based on the ontological data. In operation 280, the system calculates a response to the query based on the permissioning rules and the context. In operation 285, the system provides data to the querying user based on the calculations.

Figure 3A:
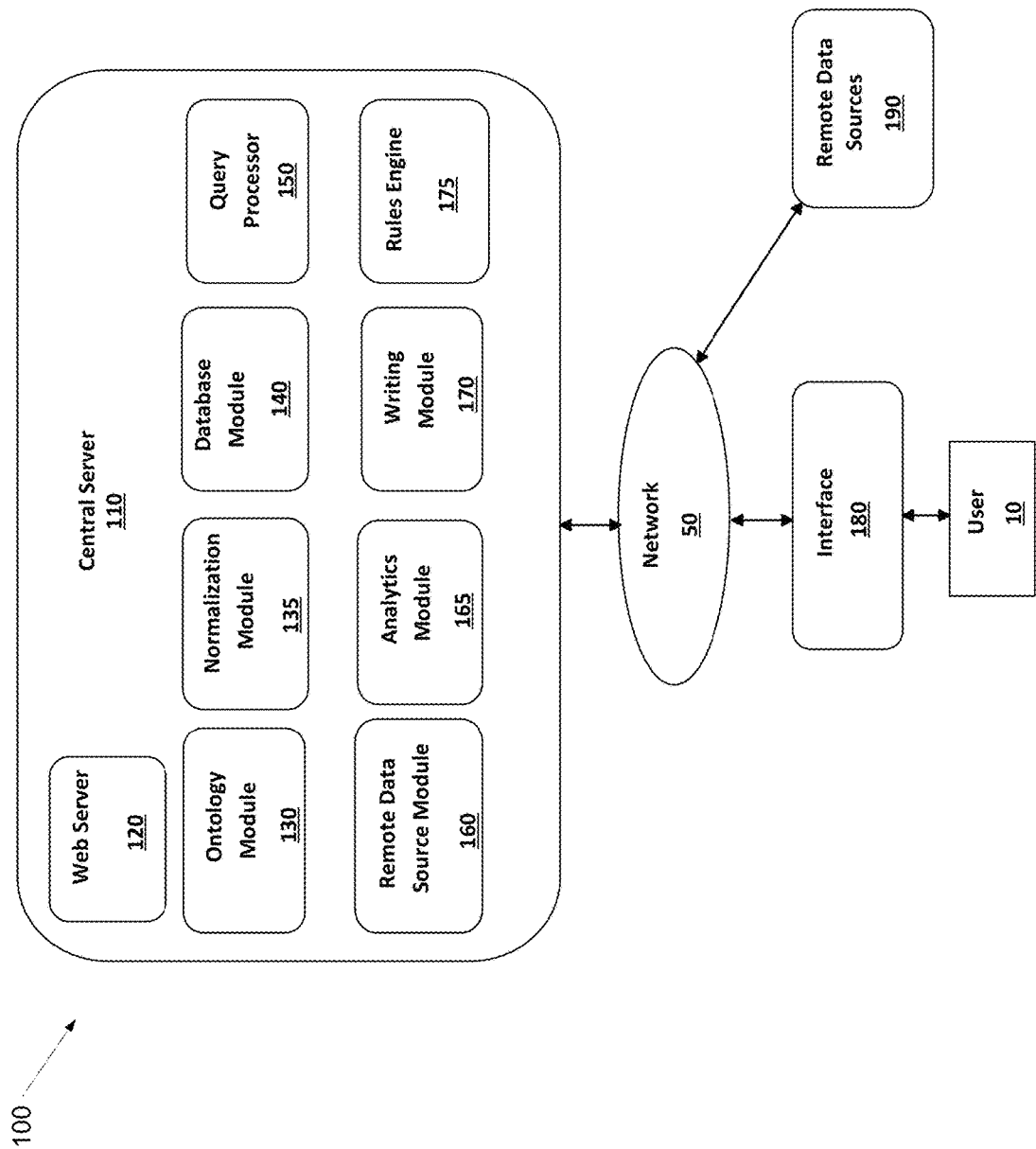
FIGS. 3A-3C are block diagrams of a system for managing multi-tiered, rule-based data permissioning, according to an embodiment of the present invention.

FIG. 3A is a block diagram of a system 100 for managing multi-tiered data permissioning according to an embodiment of the present invention. System 100 includes a central server 110 connected to a network 50. Central server 110 may be accessed by a user 10 through an interface 180, such as a user web interface or application programming interface, accessed through network 50. Additionally, remote data sources 190 may communicate with central server 110 through network 50 using remote data source module 160. Remote data sources 190 may include, but are not limited to, electronic medical records (EMR), electronic data capture (EDC), mobile devices such as Fitbit®, pharmacy data, laboratory data, or genomic data, for example. A user 10 interested in contributing data to, and/or obtaining data from system 100 may access central server 110 through remote data sources 190 accessed through network 50. Network 50 may be any type of communications network, including a public or private telephone (e.g., cellular, public switched, etc.) network and/or a computer network, such as a LAN (local area network), a WAN (wide area network), or the Internet or an intranet, that enables central server 110 to interact with users and remote data sources 190 in order to send and/or receive data and other information. The connections with network 50 may be wired or wireless connections or even a file transfer system, such as a CD, DVD, or thumb or flash drive, which contains data from the users or the data sources.

Embodiments of central server 110 may include a web server 120, an ontology module 130, a normalization module 135, a database module 140, a query processor 150, a remote data source module 160, an analytics module 165, a writing module 170, and a rules engine 175. Web server 120 may be configured to manage access to central server 110 through interface 180 for users 10. Ontology module 130 may be configured to provide ontological mapping functionality to allow user retrieval of correct data fields. Ontology module 130 may utilize in part or in full existing and future ontology tools configured to map data. Ontology module 130 may also be configured to enable manual or algorithmic reconciliation of data fields to data ontologies and may also be configured to support user-defined algorithms and creation of new fields to store the results of those algorithms. These new fields may then be shared with other users once the new fields are mapped to an ontology and rules governing permissioning are selected. Normalization module 135 may be configured to normalize differing values of data contributed by user 10 through interface 180 or remote data sources 190. Normalization module 135 may be configured to convert values to standard units (such as Fahrenheit/Kelvin/Celsius) or dictionary terms (Male/Female from M/F, etc.) and may include functionality that attempts to determine the type of data captured by a data set through the use of its data distribution. Normalization module 135 may also be configured to designate one or more ontologically-mapped data fields to "keys" which may be used to identify the same entities across data sources. For example, the social security number key may be used to identify "John Smith" across EMRs, EDC systems, and activity trackers. Database module 140 may comprise the databases that store information used by system 100. Query processor 150 may operate as the engine that processes a user's query from interface 180 and determines appropriate data to dispense by consulting database module 140 and/or remote data source module 160. (Although query processor 150 is shown in FIG. 3A as being within central server 110, it may be separate from the central server.) Remote data source module 160 may be configured to facilitate communication between system 100 and remote data source 190 to ensure system 100 is aware of user data even when such data are not located locally in system 100 to provide such data to query processor 150. Remote data source module 160 allows user 10 to query system 100 through interface 180 using query processor 150 and obtain or gather user data even when such data is located at other data sources (i.e., when system 100 functions as a broker). Remote data source module 160 may also operate using virtual database functionality known in the art, such as the commercial product, Teiid, for example.

Writing module 170 may be configured to convert written laws and/or consent agreements in order to capture and structure the logic of the laws and agreements that enable or restrict data sharing between users through query processor 150. Consent agreements and laws concerning data sharing and privacy may be coded into databases in database module 140 in the system as rules using system interfaces (e.g., user interface, web interface, or application programming interface). These rules may be coded into the system, and rule templates may be created. For example, an informed consent agreement in a clinical trial may utilize a clinical trial Sponsor's previously-entered template for informed consent. The Sponsor may conduct two clinical trials (clinical trial A and clinical trial B). In clinical trial A, the Sponsor may obtain a written consent agreement, signed by a user, to govern the Sponsor's use of user data obtained through clinical trial A. Information governing the Sponsor's use of user data contained in the written consent agreement may be loaded into system 100 and converted into rules that govern the sharing of user data obtained through clinical trial A. If, as an example, the written consent agreement contained a clause that allowed the Sponsor to share user data obtained through clinical trial A with other users (e.g., a patient's physician, another sponsor, or the FDA), the system or system administrators may convert this clause into a structured rule. Because this rule is part of a consent agreement, it will take precedence over user settings, such as a setting requiring individual requests before sharing users' clinical trial data. Prior to clinical trial B, the Sponsor may use writing module 170 to design and generate informed consent agreement templates. Writing module 170 may also code the users, data fields in question, and contextual sharing rules. Writing module 170 may also facilitate the digital signature of the agreement, future amendments to the agreement, and/or the subsequent sharing of data per the agreement.

Rules engine 175 may be configured to calculate the precedence of rules across the three rule tiers (i.e., laws, consent agreements, and individual preferences). It may also be configured to determine if potential rules within the same tier overlap according to continuous criteria such as weight and/or discrete criteria such as gender. An embodiment of a rules engine workflow is found in FIG. 8. Rules engine 175 may operate under the principle that only non-overlapping rules may be created in system 100. In such a case, before a new rule can be created, rules engine 175 may calculate if the new rule overlaps with any existing rules. If there is an overlap, rules engine 175 may inform the user of the overlapping fields and conditions, and the user may choose to update the rule, so it may then be added to the system.

There may be two steps to identifying overlap for rules. First, rules engine 175 may narrow the universe of existing rules to those that may overlap with the new rule according to the tier of the new rule. The system may include only tiers that are at or above the tier of the new rule. For example, a user preference may be compared against other user preferences as well as consent agreements and laws, consent agreements may be compared against consent agreements and laws, and laws may be compared to laws. Next, the system may narrow the universe of existing rules by the specific parameters a user enters for a new rule. These parameters may include the ontologically-mapped data fields and their sharing contexts, such as types or specific instances of requestors, contexts, entities, data sources, and date ranges, for example. The result of this step is a set of existing rules that apply to one or more of the fields to be shared. Second, for each data field to be shared, rules engine 175 may calculate whether there is overlap in the logical space covered by the new rule versus the existing rules returned in the first step. Logical space refers to specific values for discrete variables (such as gender), ranges of values for continuous variables (such as age, weight, and systolic blood pressure), and any Boolean logic (AND, NOT, OR) applied to those values. If the new rule applies to a space that is completely separate from the space covered by existing rules, rules engine 175 may determine that the new rule may be created. If the new rule overlaps with existing fields, rules engine 175 may determine that the new rule may not be created and may indicate the details of the overlap in logical spaces. Rules engine 175 may notify the user of this determination and the details of the overlap. The rule creator may then choose to adjust the new rule's parameters or contact the creator of the overlapping rule(s). Once the user resolves any overlaps and saves the rule, rules engine 175 may communicate with database module 140 to store the rule.

In some embodiments, remote data source module 160 may become aware of new instances of a user's data, such as hospital data, data from a clinical trial study in which the user participated, data uploaded by the user, or data uploaded by a medical device associated with the user, or data uploaded through remote data source 190. Remote data source module 160 may obtain or gather this data through users or devices connected to the system 100 such as remote data sources 190. Remote data source module 160 may also communicate with ontology module 130 to ensure data is presented to system 100 using a consistent ontology, allowing a user to obtain fully accurate and consistent results across different sources after issuing a query using query processor 150.

Embodiments of the system may use remote data source module 160 to ensure data from remote data sources 190 (e.g., EMR systems, EDC systems, activity trackers, or other connected devices) are identified and mapped to an ontology through ontology module 130. In such embodiments, a specific ontology may relate to a single entity type (e.g., data about a person, company, clinical trial, hospital facility, medical or consumer device, or manufacturing machine) and contain distinct data fields that describe that entity type. For example, data fields for an entity type "person" may include, but are not limited to, weight, distance walked, distance climbed, blood pressure, and blood glucose levels. Remote data source module 160 may access data from remote data sources 190 thereby permitting querying of aggregated data in real time. In contrast to the present inventions disclosed herein, existing data virtualization tools utilize a single, uniform application programming interface (API) to access data from disparate or heterogeneous databases, and do not provide for the mapping of data from external or remote sources to a target entity's ontology, or the enforcement of such an ontology (i.e., on the granular level of specific data fields, such as, for example, by using specific URLs for every data field). Existing data virtualization tools may not perform data normalization, and do not attempt to determine what a field is capturing by looking at its data distribution.

Data tools such as those found in U.S. Pat. No. 8,799,331, assigned to the applicant of this application and incorporated by reference in its entirety herein, may assist embodiments of the present invention. As an example, in the clinical trial context, a patient's weight may be called "patient-weight" and "P_W" in two different data sources. Although existing data virtualization tools may aggregate results from both sources and display data as two separate fields, embodiments of the present invention may enforce a native ontology by requiring external data fields to map to the data field of the native ontology, allowing the display of a single field that includes the data from both sources (listed, for example, as "Weight"). Additionally, if patient-weight is captured in pounds, and P_W is captured in kilograms, the system may also provide normalization of these fields into one standard unit using normalization module 135. Users may select a standard unit in their user preferences, and the system may be configured to convert all relevant measures into those standards.

Figure 3B:
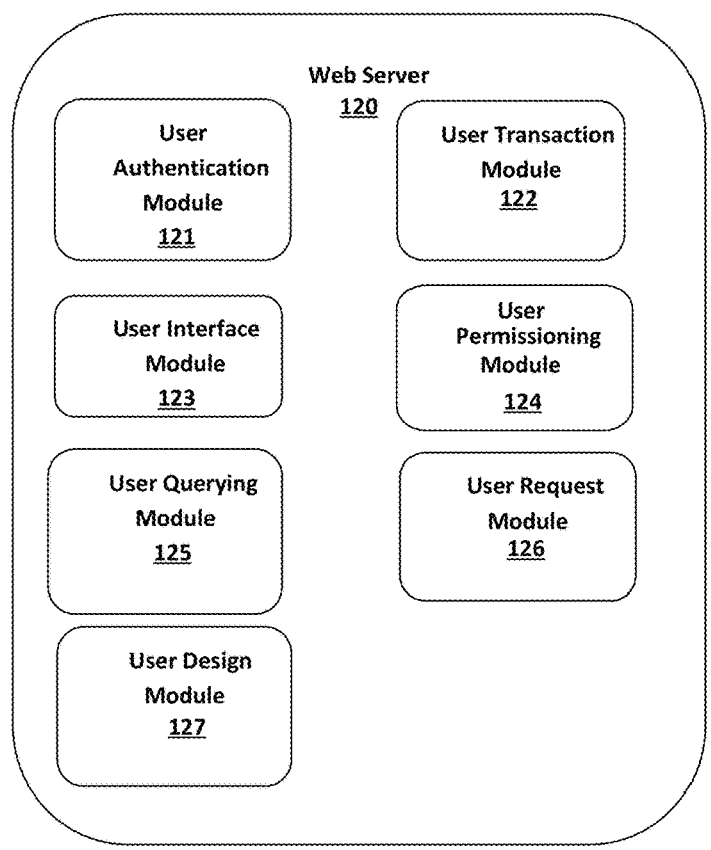

FIG. 3B is a block diagram of web server 120 used by central server 110, according to an embodiment of the present invention. Web server 120 may include a user authentication module 121, a user transaction module 122, a user interface module 123, a user permissioning module 124, a user querying module 125, a user request module 126, and a user design module 127.

User authentication module 121 may be configured to ensure that a user logging into system 100 through interface 180 has proper authentication to access the user's data. This may include verifying user names, passwords, PIN numbers, or other authentication functions. In some embodiments, user authentication module 121 may enable users to log in to access data from the system and data sources connected to the system. Consequently, the system removes the need for users to directly log in to other systems in the data ecosystem in order to share or access data. The system may also be configured with single sign-on if certain data sharing entities want to allow access to their systems for purposes other than querying of data. The system's data sharing rules may govern the data that can be shared in certain contexts.

User transaction module 122 may be configured to provide a user 10 with information regarding a history of transactions that have taken place through system 100. This may include information regarding history of user permissioning selections, user query transactions, and corresponding dates. Embodiments of user transaction module 122 may allow a user to know specific instances of when his or her data have been accessed, including the specific data and requesting user, as well as when an attempt has been made to access the user's data. User transaction module may be accessed through web server 120 using interface 180. The transactions may be stored in databases residing in database module 140.

User interface module 123 may be configured to provide a specific user interface with which a user interacts in order to access system 100, such as interface 180, which may be a user web interface, or application programming interface, for example. User interface module 123 includes interface capabilities sufficient to allow the user to interact with other user modules such as user authentication module 121, user transaction module 122, user permissioning module 124, and user request module 126, among others.

User permissioning module 124 may be configured to allow a user to set multi-tiered permissions for the data the user controls. User permissioning module 124 may provide the user with a list of data fields that system 100 associates with the user, such as, but not limited to, name, weight, gender, quality of life, blood pressure, genomic data, data from specific clinical trials, specific medical images, or medical devices, for example. When given permission, users may also control data of entity types other than "person." For example, an employee of a clinical trial sponsor may control data about the entity type "investigative sites." Data fields about this entity type may include site name, address, phone number, and available procedures. For each data field, user permissioning module 124 may provide the user with access to selectable permission rules. In some cases, however, certain rules may operate conditionally upon other rule selections. For example, some rules may not be user selectable, and may simply notify a user that he or she is subject to certain laws or agreements. Depending on the selections the user makes, certain rule options may be available or unavailable. User permissioning module 124 allows selection of rules requiring the user's permission based on the individual data sharing requests from entities, as well as selection of global settings to automatically govern requests of a certain type (such as by a specific user, specific data request, specific time periods, among others). Global settings set by users may allow a querying user to access data through remote data source module 160 or database module 140 through internal source database 147 without an individual request for the user's consent in every query instance. User selections made in user permissioning module 124 may be used to determine what individual data a user may access upon querying query processor 150.

In some embodiments, user permissioning module 124 may include default rules that govern initial access of user data before a user has input specific data-sharing permission rules. For example, a default setting may require individual requests for a user to access any of the user's data associated with the system. Where applicable, regulatory, legal, personal, or company-specific policies regarding data ownership and sharing may supersede user settings. As an example, when system 100 first becomes aware of an instance of a U.S. citizen user, that user's data-sharing permissions are automatically subject to U.S. laws stored in system 100. In some embodiments, user permissioning module 124 may be configured to provide a user options to delineate data-sharing permissioning responsibilities to another user in the system, such as the user's physician. In this way, one user may make data-sharing decisions about other users' data. Similarly, a user from a remote system who has added such system as an accessible remote data source may set data-sharing permissions on behalf of that data source.

User querying module 125 may be configured to allow a user to query system 100 for access to user data. Embodiments of user querying module 125 may allow the user to request certain data fields, such as name, weight, gender, quality of life, blood pressure, genomic sequence, or medical image such as an MRI. The requests may also be targeted, such as those made to specific users, about specific groups of users, or for data obtained from specific data-collecting medical devices (e.g., an electrocardiogram device, an activity sensor, a glucose monitor, etc.).

User querying module 125 may also be configured to provide multi-tiered search fields populated based on the content of previous entity or context selections. For example, if a requesting user selects "Clinical Trial A," the subsequent selection of data systems may display only data systems used in Clinical Trial A, and to which the user has access. Similarly, using querying module 125 to select "Person" out of a list of users restricts the list of fields available to the querying user to fields that relate to "People" and to which the querying user has permissioned access.

User querying module 125 operates through query processor 150 to query specific users or data fields based on the request and determine the permissioning rule filters selected by the users. Querying module 125 may execute the query and return a description of the data that can be shared with the querying user without individual user permission requests. When a query is performed using query processor 150, query processor 150 may search all sources known to system 100 for the types of requested fields in the query. If the data are stored by system 100, such as in user data database 141, the status of such data is always known to the system. If the data are stored virtually, the system may become aware of data changes automatically, or on demand through remote data source module 160. Data that have been added to, updated by, or removed from virtual sources known through remote data source module 160 may be known by the system at the time of query.

In some embodiments, querying module 125 may provide a requesting user with a summary of the available data based on the query. The summary may include information regarding the data immediately available without restriction versus a potentially complete data set available if the requesting user issues individual requests to users in order to access the respective data fields for the given context. For example, after a user 10 issues a query, query processor 150 may determine that individual user requests are required to access the queried data in 30% of users. User 10 may then issue data-sharing requests to those 30% of users that require individual permissioning or proceed with the available data from the remaining 70% of users (or both). If individual requests are issued, user request module 126 may issue requests to share the requested data with the requesting user. In some embodiments, query processor 150 may also utilize an analytics module 165 shown in FIG. 3A. Analytics module 165 may provide querying users information about the system's total population of user data, based on the data sharing selections made by the group of individual users. In some cases, queries with large numbers of criteria may return a small resulting population size, and the analytics module may be configured to infer missing data about patients using predictive analytics methods known in the art. The analytics module may also be configured to broker financial transactions related to exchange of user data.

User request module 126 may be configured to communicate data access requests from data requesting users to other users. User request module 126 may allow the user to select whether to provide access to the requested data in that particular instance. User request module 126 may also be configured to deliver messages to a user, both from the system or other users, through access to interface 180. These may include messages from certain users that have accessed the user's data to recommend that the user obtain certain therapies or preventive measures, messages facilitating individual requests for permission, messages enabling direct communications among users, messages notifying users of overlapping rules, or messages recommending the user for upcoming clinical trials, for example. User request module 126 may be configured to send messages to users about when rules governing their data sharing may change (e.g., users may be notified when a date is approaching that will affect user opt-out terms, allowing them opportunity to opt out before such date). In some embodiments, user request module 126 may be configured to proactively send messages to users to encourage broader data sharing, for example, by describing the potential value of the data based on demand and the potential economic benefit from queries of similar data. In some embodiments, user request module 126 may be configured to recommend data fields that users may wish to share or query based on the quality of the data and the popularity of similar fields and queries. In some embodiments, the system may broker transactions between providers and consumers of data, potentially leveraging third party vendors to facilitate payments.

In some embodiments, user request module 126 may be configured to provide messaging functionality among users, or between the system and one or more users, according to certain rule-based contexts. For example, laws and consent agreements covering messaging between physicians and patients may be coded into the system. Established relationships may exist in the system based on laws and agreements. For example, a clinical trial sponsor may contact a clinical trial participant based on rules in the participant's consent agreement. Accordingly, the system may be configured to enable creation of rules permitting user communication outside the scope of specific data fields. In some embodiments, user request module 126 may be configured to create and send automated messages when system 100 becomes aware of data that meet certain rule-based criteria. For example, user request module 126 may provide a user with a message sent in response to users that are patients who have been observed to have a heart rate above 115 beats per minute (bpm) in a clinical trial. In other embodiments, user request module 126 may be configured to send and receive notifications, such as notifications regarding financial transactions. For example, user request module 126 may be configured to allow system 100 to connect with third-party payment vendors to elicit and transfer funds, and notify users of transactions or requests for transactions. User request module 126 may also be used by a Sponsor to distribute to system users informed consent agreements, written using writing module 170 (as described above), to enroll users in one of its clinical trials.

Figure 3C:
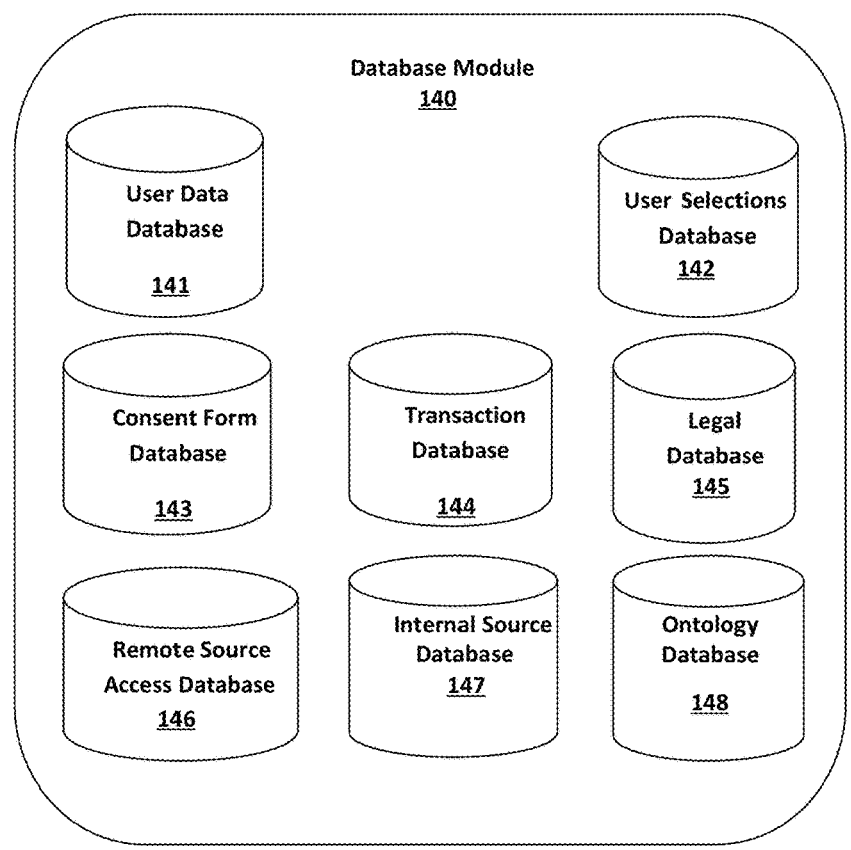

FIG. 3C is a block diagram of database module 140 used by central server 110, according to an embodiment of the present invention. Database module 140 allows central server 110 to access underlying databases in communication with system 100. Example databases include user data database 141, user selections database 142, consent form database 143, transaction database 144, legal database 145, remote source access database 146, internal source database 147, and ontology database 148. User data database 141 may include data regarding the system's users, such as user credentials and preferences. User selections database 142 may include data stored regarding user permissioning rule selections for access to the user's data. Consent form database 143 may include data from user consent forms that the system is aware of, to give consent for certain requesting users to access that user's data. Transaction database 144 may store transaction data, including for example, instances of queries, data access, user permissioning modifications, or individual requests. Legal database 145 may include data regarding current laws that restrict, allow, or mandate the sharing of user data. Legal database 145, consent form database 143, and user selections database 142 may all be configured to store groups of rules generated and/or arranged by rules engine 175 and obtain data from rules engine 175. Remote source access database 146 may include authentication information for remote data sources, as well as field names and locations in those remote sources. Internal source database 147 may store queryable data directly in the system, such that the data need not be accessed remotely. Ontology database 148 may be configured to store ontologies and entity type ontology field mappings for both internal and remote sources. In instances where ontology database 148 stores mappings for remote sources, ontology database 148 may reference data stored in remote source access database 146. Although database module 140 is shown in FIG. 3A as being within central server 110, it may be separate from the central server.

The parts, blocks, and modules shown in FIGS. 3A-3C are examples of parts that may comprise system 100, central server 110, web server 120, and database module 140, and do not limit the parts or modules that may be included in or connected to or associated with system 100 and these other servers and modules. Thus, although many modules are shown as being within central server 110, certain modules may be distinct from central server 110, and may have their own processor and associated hardware.

Figure 6:
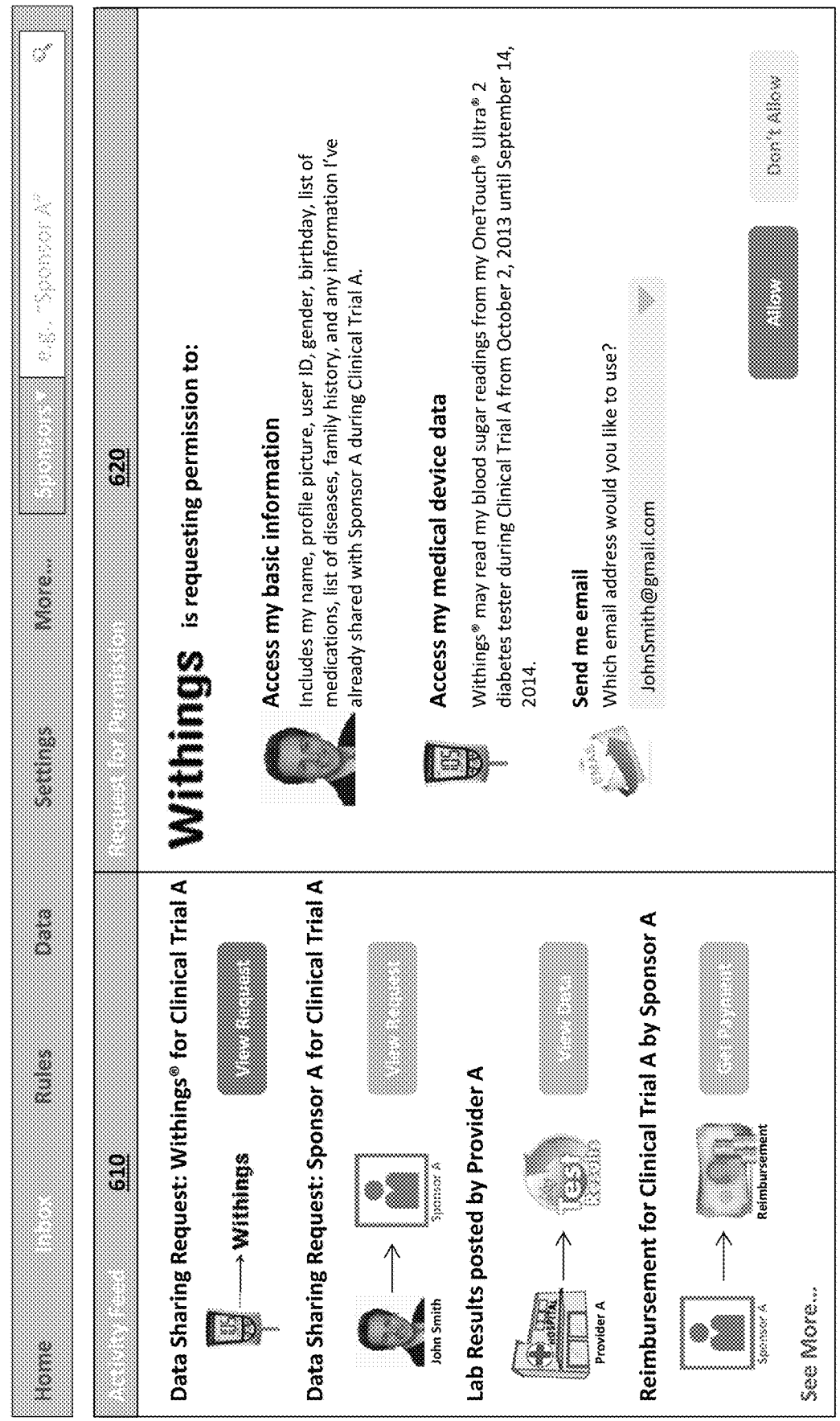
FIG. 6 is an example request interface, according to an embodiment of the present invention.

FIGS. 4, 5, and 6 are examples of user interfaces used with system 100. FIG. 4 is an example of a query interface 400 configured to allow a requesting user 10 to issue a query for user data, such as by using user querying module 125, according to an embodiment of the present invention. Query interface 400 may be accessed through interface 180. Query interface 400 may include Context Type filter 405, which may be a drop-down filter, for user 10 to select the type of context of the data it wishes to query. Context types may include clinical trials, hospital visits, patient's homes, and manufacturing processes, for example. Query interface 400 may include Context filter 410, which may be a drop-down filter, for user 10 to select at least one specific context, such as "Clinical Trial A," "Visit A," "Residence A," and "Manufacturing Process A." Query interface 400 may include an Entity Type filter 415, which may be a drop-down filter, for user 10 to select the type of entity it wishes to query. Entity types may be people, places, or things about which data are generated or queried, which may include "Patients," "Sponsors," "Providers," "Drugs," "Medical Devices," and "Manufacturing Facilities," for example. Query interface 400 may include an Entity filter 420, which may be a drop-down filter, for user 10 to select at least one specific entity about which data are generated or queried, such as "John Smith," "Sponsor A," "Provider A," "Drug A," "Medical Device A," or "Manufacturing Facility A," for example. The system may be configured so that only the types of entities about which data are generated in a given context are displayed. For example, data may not be generated about manufacturing facilities during clinical trials. Accordingly, if "Clinical Trial" is selected as the Context Type, manufacturing facilities would not appear in the Entity Type or Entity filters. Query interface 400 may include a date range selection 425 configured to allow a user to select a specific date range for user data it wishes to query. Query interface 400 may include a Data Source filter 430, which may be a drop down filter, for a user to select specific sources of user data it wishes to query from. As shown in FIG. 4, data sources may include electronic data capture (EDC) systems, electronic medical record (EMR) systems, payor databases, pharmacy databases, laboratory databases, or genomic databases, among others.

Query interface 400 may also include preview window 440, configured to display to the querying user the user data accessible based on the current status of the user's query selections. Preview window 440 may include additional features such as a target user calculator 441, which is configured to display the total number of unique target users that may be subject to the data query based on the user's filter selections. Preview window 440 may include a field filter 442 configured to display specific data fields associated with the entities selected for query. Field filter 442 may be configured with selection capability, to allow user 10 to select or de-select certain user data fields from the query. Field filter 442 may display data fields (e.g., for entity type: Clinical Trial Patient) such as name, weight, age, gender, quality of life, genomic sequence, blood pressure, address, phone number, social security number, medications, and lab test results, for example. Preview window 440 may include a range filter 443, configured to allow user 10 to select, de-select, define, or otherwise limit the user data queried based on specific ranges or values of data fields. For example, a requesting user could de-select "male" from the range filter and its query would be limited to females that meet the remaining specifications, such as target, context, data source, and date range. Preview window 440 may include data access display 445, which is configured to display the data accessible to a querying user based on the user's selections. For example, data access display 445 may be configured to display separate columns for (i) records of user data that are automatically accessible to the requesting user upon query, (ii) records of user data that are accessible to the requesting user only by obtaining permission through individualized or manual request, and (iii) records of user data that are not accessible to the user under any circumstances. Query interface 400 may also include a view results link 447 configured to display the results of any automatically accessible user data to the querying entity based on the querying user's query. Query interface 400 may also include a send requests link 448 configured to send data access request messages to users whose data is accessible only by individual permissioned requests. Query interface 400 may also include a view/edit rules link 449 configured to display visible rules that govern a requesting user's query based on the query conditions selected. In some embodiments, user 10 may view rule definitions as programmed into the system if the rules are visible to the requesting user. User 10 may also edit or delete existing rules or create new rules, based on permissions.

FIG. 5 is an example rule creation interface 500, according to an embodiment of the present invention. Rule creation interface 500 may be configured to allow a rule creator, such as a user 10, to create rules that govern the permissions for sharing of their data to others. In particular, a user 10 may create rules regarding the sharing of their specific data fields while a data provider user or system administrator may create rules regarding specific consent agreements or laws that exist governing the sharing of user data fields. When a query is issued, such as through query interface 400, query processor 150 may read rules created through rule creation interface 500 to determine whether the requested data can be provided to the querying entity. Rule creation interface 500 may be configured to define the rule name 505, which allows a rule creator to name the rule being created. Rule creation interface 500 may be configured to define the querying requestors 510 that are permitted to view defined data of the rule creator. For example, a rule creator may configure a rule such that only Clinical Trial Sponsor A may view the user's data. Rule creation interface 500 may be configured to define the context type 515 and context 520 in which a requesting user may view data. For example, a rule creator may create a rule allowing the sharing of data associated only with Clinical Trial A in which the rule creator participated. Rule creation interface 500 may be configured to define the entity type 525 and entity 530 to include in the query. Additional contexts may include date range 535 for which data may be made available. Rule creation interface 500 may also include a rule overlap link 540 to allow the resolution between the new rule and existing overlapping rules within the same rule tier. For example, a consent agreement for Sponsor A and John Smith in any clinical trial may overlap with a new consent agreement for Sponsor A and John Smith in Clinical Trial A.

Rule creation interface 500 may also include data selection window 550. Data selection window 550 may be configured to receive input of specific data sources and data fields that a rule creator would like the defined rule to govern. Accordingly, data selection window 550 may include data source configuration 555 that would allow the rule creator to assign the rule to data associated with specific data sources, such as, for example, EDC systems, EMR systems, payor databases, pharmacy databases, lab databases, and genomic databases. Data selection window 550 may also include data field configuration 557 that would allow the rule creator to assign the rule to specific data fields, such as, for example, name, weight, gender, age, quality of life surveys, or genomic sequences.

Rule creation interface 500 may also include action assignment window 560. Action assignment window 560 may be configured to receive input of the user required to approve requests for data sharing, and may be configured to receive selection of the type of approval required to facilitate data sharing, such as automatic sharing or individualized/manual requests, for example. When rule creation interface 500 is configured with the rule creator's desired configurations, the rule creator may create the rule to be stored by the system and associated with the specified data fields, using a save rule link 570. In some cases, rule creation interface 500 may be configured to set the visibility of a rule such that the rule may or may not be visible to different types of users, using visibility link 580.

FIG. 6 is an example request interface 600, according to an embodiment of the present invention. Request interface 600 may be configured to allow a user 10 to view, manage, and send messages through user request module 126, as well as view the history of queries, data access, transactions, and other events associated with user 10. Request interface 600 may be configured to include an activity feed 610, which can display messages sent to the user, data-sharing permission requests sent to the user, lab results posted by hospitals, physicians, as well as medical reimbursement transactions, for example. In some embodiments, system 100 may broker financial transactions, working with third-party payment vendors to elicit and transfer funds, and then notify users of transactions or requests for transactions through activity feed 610 in request interface 600.

Request interface 600 may also include a message window 620 configured to display the content of messages, requests, and other information sent to user 10. User 10 may use message window 620 to view specific data access permission requests from specific entities, and determine whether to allow or deny user access to the data fields requested by such user. In some embodiments, system 100 may be configured to recommend data fields that users may wish to share based on the popularity and quality of data of similar fields and queries, or data fields shared by other users, and may deliver these suggestions through request interface 600.

Figure 7:
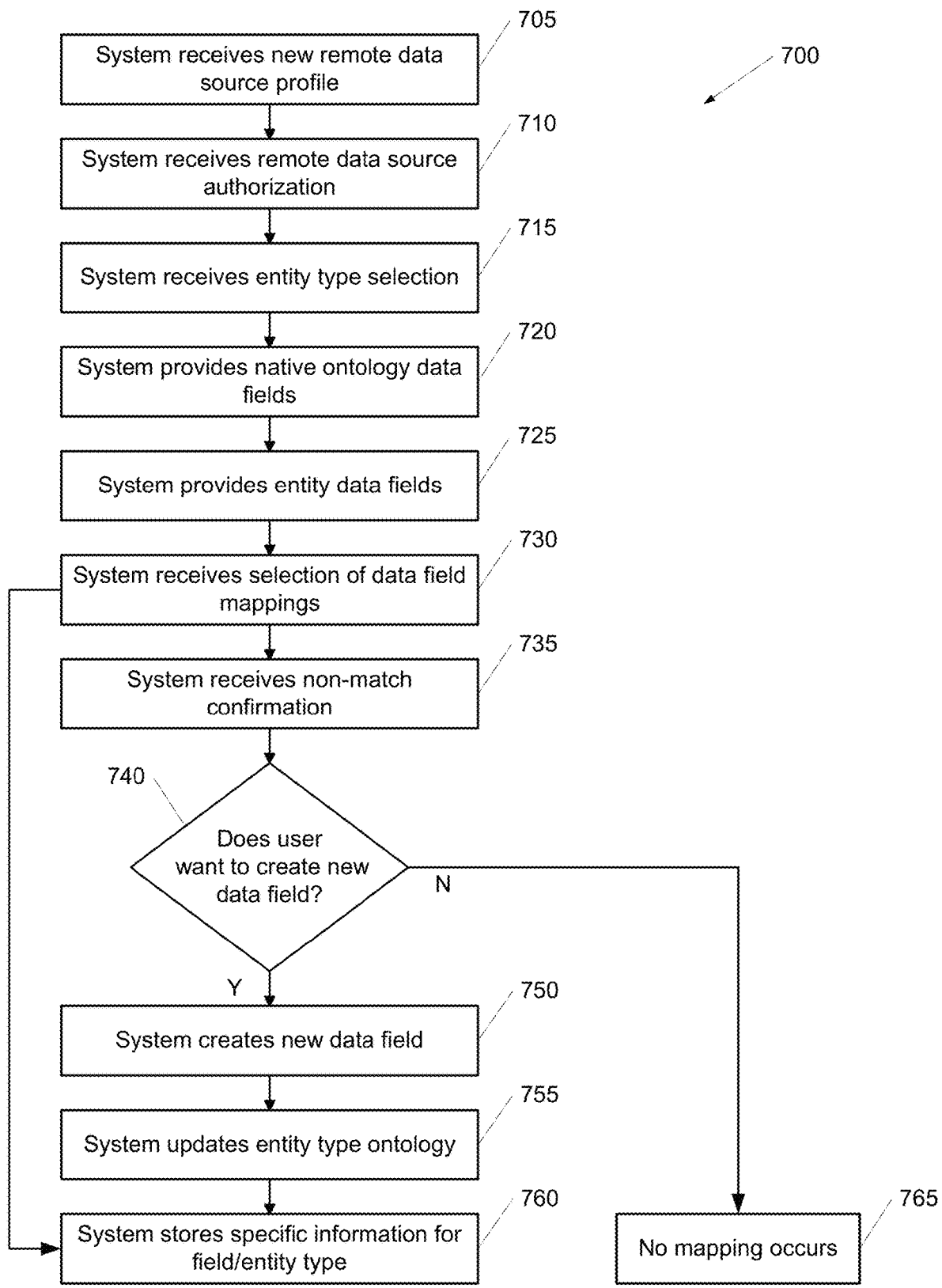
FIG. 7 is a flowchart of a data ontology mapping workflow, according to an embodiment of the present invention.
Figure 8:
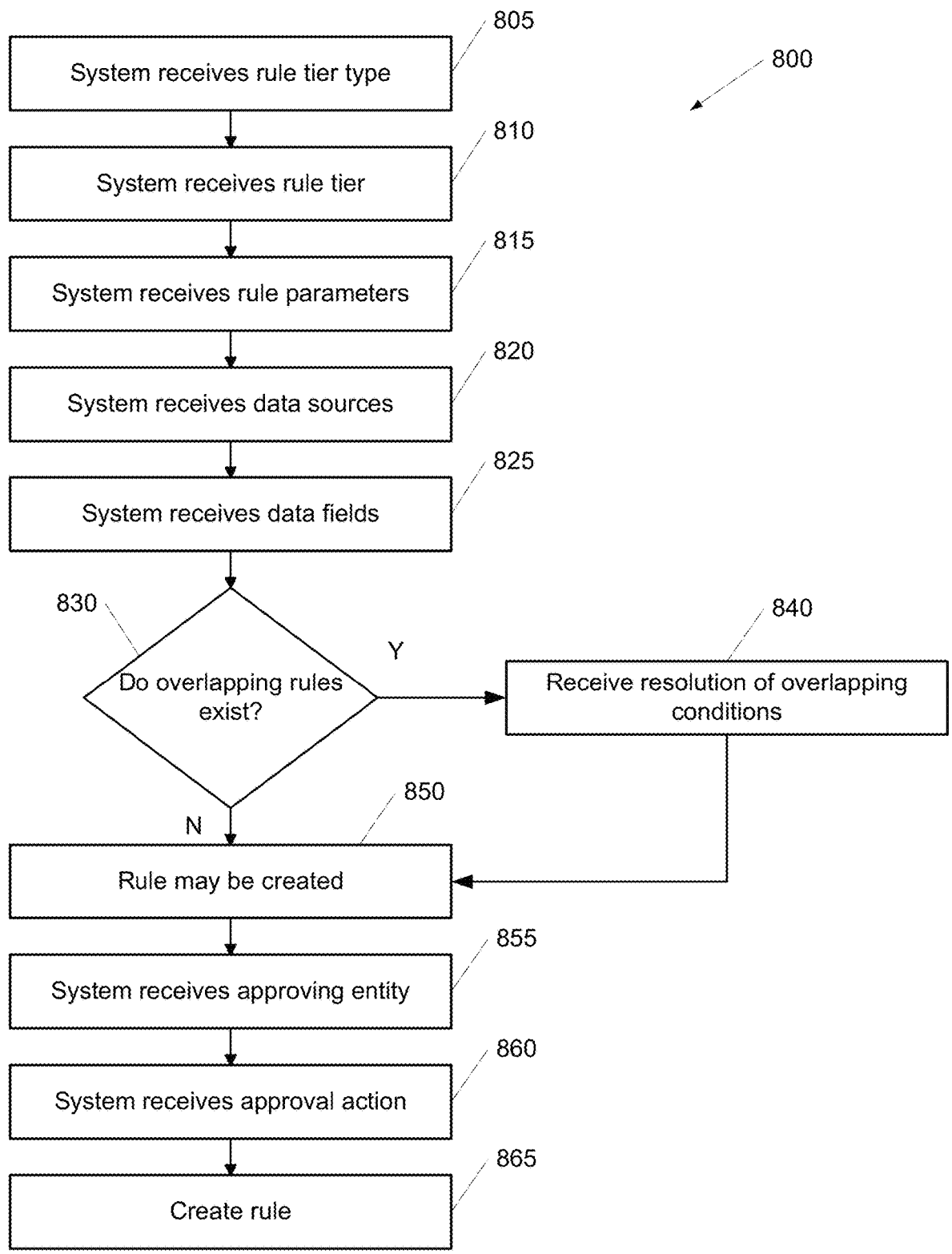
FIG. 8 is a flowchart of a rule creation workflow, according to an embodiment of the present invention.
Figure 9:
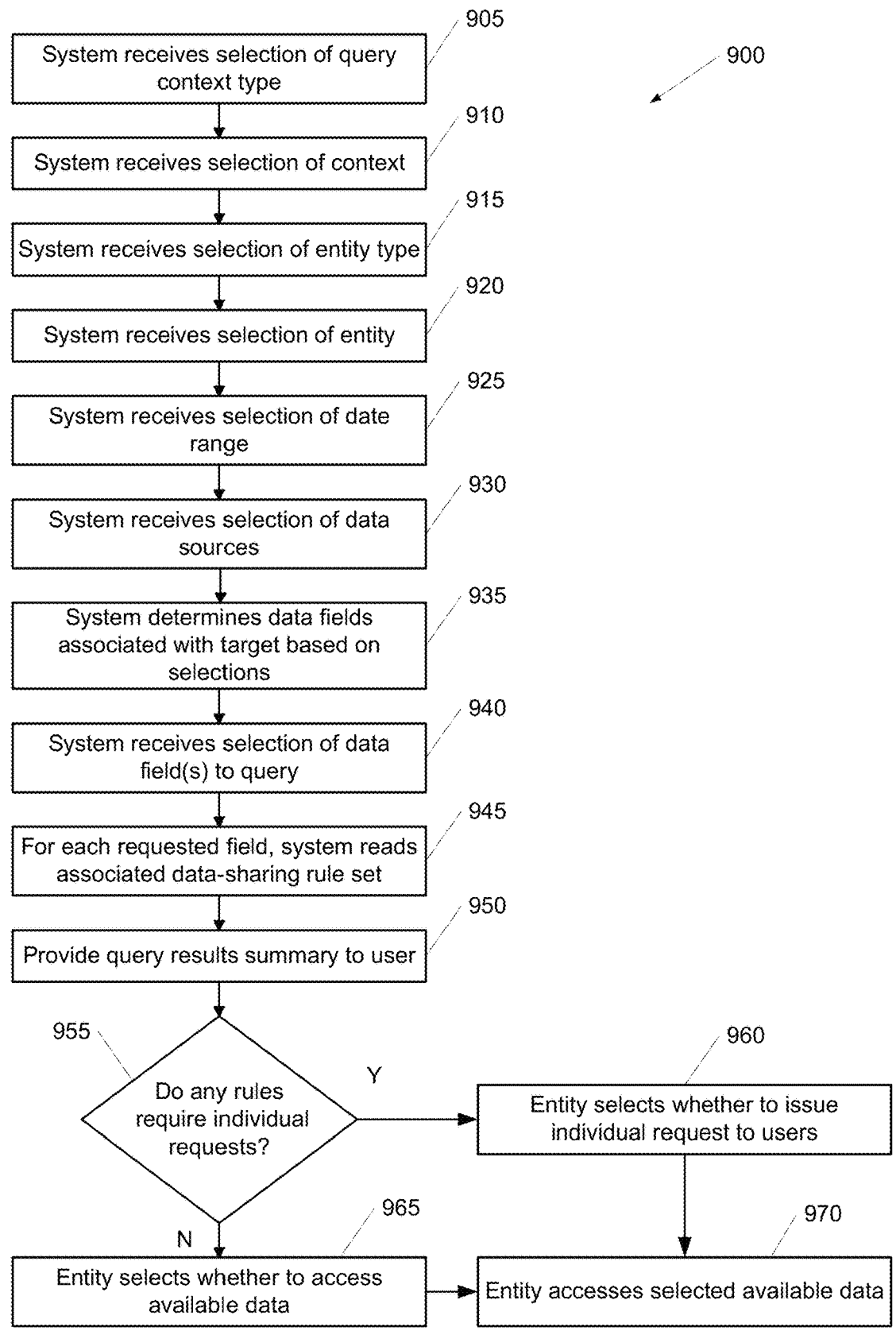
FIG. 9 is a flowchart of a data query workflow, according to an embodiment of the present invention.

FIGS. 7, 8, and 9 are examples of flowcharts used with system 100. FIG. 7 is a flowchart of a data ontology mapping workflow 700, according to an embodiment of the present invention. In operation 705, a user 10 having a data source external to the data source of the native system creates a specific, corresponding entity in the system, such as a new remote data source profile. The entity may also provide its application programming interface (API) to give remote data source module 160 access to its data source, or an administrator of the system may obtain the API. In operation 710, central server 110 may utilize remote data source module 160 to establish an authorization mechanism for access to the remote data source, whereby data may be repeatedly and securely accessed by system 100 (e.g., with login and password, public/private key-based authorization, etc.). System 100 may use remote data source module 160 so that users and administrators of system 100 may access data through interfaces 180 associated with system 100, rather than through direct access to the data source. In operation 715, the system provides a user interface for selection of entity types and receives the user's selection of its entity type. In operation 720, system 100 provides data fields of a native ontology corresponding to the selected entity type. In operation 725, system 100 provides an interface for a user to input data fields specific to that entity. In operation 730, ontology module 130 receives the user's selection of a correspondence or mapping between each native ontology data field and each entity's data fields. Where entity data fields match data fields in the system's ontology, the process proceeds to operation 760. Where a data field does not have a corresponding native data field in the system's ontology, the user may confirm a non-match in operation 735. From there, the user may determine whether to create a new data field in the ontology at issue, in operation 740. If the user chooses not to create a new data field in the ontology, no data mapping occurs, as shown in operation 765. Non-mapped data may be added to the system, and users who add non-mapped data may always access such data, but such data may not be accessible by other users. If the user chooses to create a new data field and a system administrator approves, a new native data field is created in system 100 (operation 750) using ontology module 130 and the entity type ontology is updated accordingly (operation 755). When fields from data sources have been ontologically mapped, in operation 760 system 100 may use remote source access database 146 or internal source database 147 to store information (such as a URL). This mapping allows for the cross-entity querying described herein. In some embodiments, if a user does not have sufficient system rights to create a new data field, the user may contact a system administrator to have such data field added.

Newly created data fields may be subject to the intersection of rules that relate to component fields. For example, two rules may indicate that a Number of Steps (e.g., from an activity tracker) may be shared with Sponsor A in Clinical Trial A, and Hemoglobin A1C may be shared with anyone in any context. Sponsor A may receive both fields in Clinical Trial A and calculate Number of Steps/Hemoglobin A1C. As a result of these two rules, only Sponsor A may access this new field in Clinical Trial A. In order for Sponsor A to access the data for the new field for use as a benchmark or reference for Clinical Trial B, or to share this data with Sponsor B, Sponsor A would need to request permission from the owner(s) of the component fields.

In some embodiments, ontology module 130 may be configured such that one default ontology exists for every entity type in the system. This may be used for the purpose of querying unless other existing ontologies are specifically requested. An entity type's ontology may comprise fields that are material to that entity, and data types for each field, optionally including unit types. For example, the "Person" entity may include data fields called "FirstName," "LastName," and "Weight," which have data types "string," "string," and "float" respectively. The "Weight" field may also include a unit type called "pounds." Ontology module 130 may be configured to convert standard units and apply a default if no units are selected.

In some embodiments, system 100 may support the creation of new data fields through analysis or combination with existing fields. New data fields may be owned by and/or associated with the user who created it. In order for the owner of the new field to create data sharing rules associated with the data field and for the field to be accessible by users, the new field must be mapped to an ontology. For example, Clinical Trial Sponsor A may collect activity data about user John Smith using an activity tracker (e.g., Fitbit®), which may be linked to Sponsor A's EDC system in Clinical Trial A. According to Sponsor A's informed consent rules, John Smith may allow Sponsor A to view de-identified activity data from Clinical Trial A. Separately, Healthcare Provider A may collect John Smith's Hemoglobin A1C (HbA1C) test results in its EMR system. According to Provider A's consent rules, John Smith may allow Provider A to view HbA1C results and John Smith's name. Following participation in Clinical Trial A, John Smith may wish to share the data from the clinical trial with his physician at Provider A. John Smith may create a conditional rule in the system indicating that any data from Clinical Trial A may be shared with Provider A. Provider A may then use the system to access a consolidated view of activity data from the activity tracker or EDC systems in Clinical Trial A plus his name and the HbA1C results from Provider A's EMR system.

Additionally, a data analyst at Provider A may wish to create a new, derived data field relating HbA1C with activity data. However, Provider A's EMR system may not support the collection of activity data, and the Provider's EDC system may not support the collection of HbA1C data. The data analyst may use the system to create the new field for the analyst's use. The analyst may then populate the new derived data field using other queries about other patients in other contexts, so long as the analyst has access (following up with individual requests as needed). Accordingly, embodiments of the system may enable a consolidated view of data about any entity across sources, regardless of whether the underlying sources can support that view themselves. Consequently, the system may enable a commercial data marketplace for the creation and exchange of new medical knowledge.

FIG. 8 is a flowchart of a data sharing rule creation workflow 800, according to an embodiment of the present invention. In operation 805, the process may begin by the system receiving from user 10 a rule tier, such as a law, consent agreement, or user preference. In operation 810, the system receives a selection of rule tier, such as the rule within the specific instance of rule-tier type. User 10 may either create a new rule-tier type (i.e., a law, consent agreement, or preference), or apply the new rule to an existing grouping to which the user has permission. In operation 815, a rule creator inputs parameters for the rule, including the rule name, requestor type, context type, context, entity type, entity, and date range, for example. In operation 820, the rule creator may select the relevant data sources associated with the rule, such as certain EDC systems, EMR systems, payor databases, pharmacy databases, lab databases, mobile device databases, or genomic databases, for example. In operation 825, the rule creator may select the relevant data fields associated with the rule, such as certain name, weight, gender, age, quality of life, or genomic sequences, for example. In operation 830, the system determines whether any rules exist that overlap with the new rule within the same rule tier. This may be accomplished using rules engine 175. If the new rule overlaps with one or more existing rules within its tier, the rule creator must edit or discard the new rule or contact the creator of the existing rule(s) to resolve overlaps through the system (operation 840). For example, a rule may contain one or more conditions relating to the one or more fields that are part of the selected ontology. One condition may refer to a set of logical choices about one or more fields in the rule that may overlap. For one field, an overlap may refer to either the selection of the same value from a discrete set of values (such as male from male/female), or an overlap in range from a continuous variable (such as weight >150 lbs.). Once no conflicting rules exist, the system determines in operation 850 that the rule may be created. In operation 855, the rule creator may select the approving user or entity to approve whether to provide data access permission. In operation 860, the rule creator may select the Approval Action, such as whether a query for user data is automatically permitted or requires an individual or manual request to be submitted to the user, for example. In operation 865, the rule may be created. In some embodiments, the rule may be configured with view and edit permissions, such as to allow certain users varying rights to view or edit the rule. In other embodiments, a user may copy rules across contexts. For example, a user may apply existing rules and rule tiers to create new consent agreements for a clinical trial. When a rule is copied into a new context, it cannot be saved until no overlapping rules exist.

System 100 may be configured such that rules created through rule creation interface 500 are subject to certain specified boundaries. In some embodiments of the invention, rules may cover one or more data fields, and may be global, time-bound, contextual, conditional, and/or specific to one particular agreement. Rules may be 20 combined into a data-sharing rule set that contributes to the total decision-making process for data access. In some embodiments, rules may be applied differently to different data fields depending on specific sharing contexts (e.g., age and gender may be shared automatically by default to all users, while genomic data may be shared automatically with governments by law, by individual request with Sponsor A due to consent agreement, and never to other entities, according to user-defined preferences).

Government agencies may create laws, data providers and data requestors may create consent agreements, and individual users may create individual preferences surrounding their data. A system administrator may control the rules and logic of system 100. For example, if a government body is not yet a user of the system, the administrator may code laws into the system. If a government body becomes a user or entity, it may gain control over such rules. System administrator control may enable laws, consent agreements, and individual preferences to be initially coded into the system prior to user acquisition. The system rules may be configured in the following hierarchy: Laws supersede consent agreements, and both laws and consent agreements supersede individual preferences. Rules that contradict laws may not be created. Consent agreements that contradict each other regarding specific data fields with a specific sharing context may not be created unless all owners of those data field in those sharing contexts resolve the overlapping rules.

In some embodiments, when a user 10 or system administrator attempts to create a new rule, system 100 may be configured with rules engine 175 to determine whether this rule overlaps with other rules within the same rule tier. If overlaps exist, the rule's precedence within each overlapping rule context must be defined. In some embodiments, this may result in creation of separate rules in each context. For example, system 100 may create as many as four contexts concerning the binary yes/no variables of "pregnancy status" and "has had chicken pox." The precedence of a new, overlapping rule that covers data from these two variables would have to be determined in each of those contexts before the system will recognize it. There may also be overlaps with non-discrete, continuous variables, such as age. If a rule exists for men over the age of 65, and a new rule is desired for men over the age of 50, the system will not allow the rule to be added until rule precedence is defined in the overlapping context of men ages 65 and up.

In some embodiments, the system may facilitate the resolution of conflicting rules across rule tiers. For example, a consent agreement entered into the system that mandates user data to be automatically shared with Clinical Trial Sponsor A may override an individual user preference requiring individual requests before data are shared with Clinical Trial Sponsor A. Similarly, HIPAA (the Health Insurance Portability and Accountability Act) may define data fields as personally-identifiable information (PII) and legally require a patient's consent for such data fields to be shared. A government body or system administrator may code HIPAA into system 100 as rules. Healthcare Provider A may attempt to create a rule in the system for a consent agreement enabling any Clinical Trial Sponsor to obtain any patient's PII for any clinical trial. Accordingly, system 100 may alert Healthcare Provider A that its rule contradicts HIPAA and that HIPAA cannot be overridden. In some embodiments, the system may resolve system-generated communication rules. As an example, Clinical Trial Sponsor A may be running three clinical trials, 1, 2 and 3. Trial 1 may contain a rule that alerts a trial investigator (by sharing the patient's data) when a patient's heart rate is above 110 bpm. Trial 2 may contain a rule that alerts a trial investigator when a patient's heart rate is above 120 bpm. Sponsor A may attempt to create a rule that alerts a trial investigator only when a patient's bpm is over 115 for any trial. System 100 may identify the data field in the rule (heart rate), the context (any clinical trial run by Sponsor A), and check for overlapping rules. Accordingly, system 100 finds two rules covering the same data fields. Sponsor A may be alerted to this overlap, and must determine how to apply the new rule by reconciling the overlap, either across all trials using 115 bpm by superseding the existing rule for Trial 1, or in all trials except Trial 1.

In some embodiments, the system may facilitate the resolution of overlapping rules within the same rule tier. As an example, user John Smith has created an individual preference rule stating that his approval is required for use of his weight information by any entity. He later attempts to create a rule stating he will freely share his weight information with his healthcare provider (Provider A) because of an incentive it has implemented that reduces his out-of-pocket costs through data sharing. System 100 through rules engine 175 recognizes the existing overlapping rule and alerts John Smith that he must make an exception to the previous rule. If he does, any request for his weight information will require his approval unless it comes from Provider A.

FIG. 9 is a flowchart of a query workflow through the use of multi-tiered data permissioning, according to an embodiment of the present invention. Query processor module 150 determines permissions for access to user data based on a data-sharing realization process 900. To begin data-sharing realization process 900, the system receives input of context type in operation 905. The system then receives input of the context available given the selected context type (operation 910). The system then receives input of entity type in the selected context (operation 915). The system then receives input of an entity given the selected entity type (operation 920). Embodiments of the system may then receive selection of a date range (operation 925). The system then receives selection of data sources to query given the selected context and entity (operation 930). The system may then determine and display data fields and the ranges of values of those data fields associated with the targeted user based on the contexts selected for query (operation 935).

In some embodiments, the system may perform entity resolution across relevant data sources via normalization module 135 so that query results are representative of the same entity. The querying entity may then provide and receive a user's selections of specific data fields and/or ranges of values of those data fields in order to narrow or expand the data queried (operation 940). For each field, the system then reads the data sharing rules governed by law, set by consent agreements signed by users (or other entities on their behalf), or set by users (or other users on their behalf) (operation 945). The system may provide a summary of results to the user (including, for example, the number of total possible results and the percentage of hits for each requested field) (operation 950). The querying user may then freely access this information. When the system returns that individual user requests are required for a portion of the data fields (operation 955) (e.g., gender and age fields are accessible but genomic data requires permission from the user), the querying user may choose whether to send individual notification requests (operation 960) for the remaining data. These notifications may contain descriptions and restrictions, which include (but are not limited to) requesting entity name, data fields, duration of access, use case/purpose of request, and digital signature for user to accept or reject the request (e.g., Sponsor A is requesting gender, age, and genomics data fields for three years for clinical trial A). The user's response to these requests will determine whether the user may access the particular data fields (operation 965). The user may then access any selected available data that are both provided automatically in the query and permissioned by the user via notification request (operation 970). In some embodiments of the invention, the query may be optionally saved for future use.

Besides the operations shown in FIGS. 7-9, other operations or series of operations may be contemplated for workflows to be used within system 100. Data may be aggregated from disparate sources, the data may be mapped to various labels or ontologies, and the data may then be shared or permissioned to different entities. Moreover, the actual orders of the operations in the flow diagrams are not intended to be limiting, and the operations may be performed in any practical order.

Some of the benefits of the present invention include providing customizable, user-defined data access permissioning at a granular level. The system also protects sensitive data and allows an individual or organization to have control over its associated data.

Aspects of the present invention may be embodied in the form of a system, a computer program product, or a method. Similarly, aspects of the present invention may be embodied as hardware, software, or a combination of both. Aspects of the present invention may be embodied as a computer program product saved on one or more computer-readable media in the form of computer-readable program code embodied thereon.

For example, the computer-readable medium may be a computer-readable signal medium or a computer-readable storage medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, wherein the computer-usable medium contains a set of instructions, and wherein the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A computer-based method for generating a data-sharing database based on multi-tier permissioning, comprising:
   storing in the database at least one rule regarding sharing of clinical trial data, wherein the rule is based on three rule tiers, a law tier, an informed consent agreement tier, and a user preference tier, wherein a rules engine is configured to calculate the precedence of rules across the three rule tiers;

generating an informed consent agreement regarding sharing of clinical trial data, wherein the informed consent agreement is obtained by a sponsor, signed by a patient, stored in the database, and converted into structured hierarchical rules that govern the sharing of the patient data obtained in the clinical trial, and supersedes user preferences;

receiving a context-specific rule configuration comprising a context, a data source, and an entity type, wherein said context-specific rule configuration comprises at least one term of said informed consent agreement;

identifying any conflict between the context-specific rule configuration by identifying any overlapping rules within the informed consent agreement tier and resolving the overlapping rules;

determining whether the identified conflict is between a term of said informed consent agreement and a user preference and, based on the determination, resolving the conflict in favor of the term of said informed consent agreement;

determining whether the identified conflict is between terms of informed consent agreements or is between user preferences and, based on the determination, receiving resolution of the conflict;

storing said context-specific rule configuration in the database;

generating a query interface comprising a plurality of filters comprising at least the context, the data source, and the entity type;

displaying on the query interface a summary of records, satisfying the filters, that are automatically accessible to a database user, accessible by request by the database user, and outside the query context; and providing, based on the summary of records, for the database user to view the records that are automatically accessible, to submit a request for access to the records accessible by request, to view rules that govern the database user's query, and to edit or delete the rules.

2. The method of claim 1, further comprising:

receiving a data access query from a user;

determining the context to query based on said data access query receipt; and providing said user access to entity data based on said context-specific rule configuration.

3. The method of claim 1, wherein receiving resolution of the conflict comprises (i) editing said context-specific rule configuration or (ii) contacting a creator of the conflicting rule.

4. The method of claim 1, further comprising determining whether any queried data fields require access permission.

5. The method of claim 4, wherein said determining whether any queried data fields require access permission includes issuing requests for data access.

6. The method of claim 1, further comprising receiving at least one conditional rule selection.

7. The method of claim 1, further comprising storing transactions in a database.

8. The method of claim 1, wherein said context-specific rule configuration comprises a law.

9. The method of claim 1, wherein the different levels of access comprise accessibility without an access permission request and accessibility with an access permission request.

10. The method of claim 9, further comprising displaying the records satisfying the filters and that are accessible without an access permission request.

11. A computer-based method for generating a data-sharing database based on multi-tier permissioning, comprising:

storing in the database at least one rule regarding sharing of clinical trial data, wherein the rule is based on three rule tiers, a law tier, an informed consent agreement tier, and a user preference tier, wherein a rules engine is configured to calculate the precedence of rules across the three rule tiers;

generating an informed consent agreement regarding sharing of clinical trial data, wherein the informed consent agreement is obtained by a sponsor, signed by a patient, stored in the database, and converted into structured hierarchical rules that govern the sharing of the patient data obtained in the clinical trial, and supersedes user preferences;

receiving a context-specific rule configuration comprising a context, a data source, and an entity type, wherein said context-specific rule configuration comprises at least one term of said informed consent agreement;

identifying any conflict between the context-specific rule configuration by identifying any overlapping rules within the informed consent agreement tier and resolving the overlapping rules;

determining whether the identified conflict is between a term of said informed consent agreement and a user preference and, based on the determination, resolving the conflict in favor of the term of said informed consent agreement;

determining whether the identified conflict is between terms of informed consent agreements or is between user preferences and, based on the determination, receiving resolution of the conflict;

storing said context-specific rule configuration in the database;

generating a query interface comprising a plurality of filters comprising at least the context, the data source, and the entity type;

displaying on the query interface a summary of records, satisfying the filters, that are automatically accessible to a database user, accessible by request by the database user, and outside the query context; and showing, based on the summary of records, the database user the records that are automatically accessible.

* * * * *